United States Patent
Ayame et al.

(10) Patent No.: US 6,932,762 B2
(45) Date of Patent: Aug. 23, 2005

(54) ENDOSCOPE HAVING RED COMPONENT CUT FILTER

(75) Inventors: Daisuke Ayame, Saitama (JP); Mitsuru Higuchi, Saitama (JP); Kazunori Abe, Saitama (JP); Shinji Takeuchi, Saitama (JP)

(73) Assignee: Fujinon Corporation, Saitama (JP)

( * ) Notice: Subject to any disclaimer, the term of this patent is extended or adjusted under 35 U.S.C. 154(b) by 228 days.

(21) Appl. No.: 10/244,632

(22) Filed: Sep. 17, 2002

(65) Prior Publication Data

US 2003/0060684 A1 Mar. 27, 2003

(30) Foreign Application Priority Data

Sep. 21, 2001 (JP) .................................. 2001-288182
Sep. 27, 2001 (JP) .................................. 2001-295270

(51) Int. Cl.[7] .............................................. A61B 1/07
(52) U.S. Cl. ...................................... 600/181; 600/178
(58) Field of Search ............................... 600/181, 178, 600/182, 476, 478; 348/342

(56) References Cited

U.S. PATENT DOCUMENTS

| | | | | |
|---|---|---|---|---|
| 4,685,451 A | * | 8/1987 | Ando .......................... | 600/181 |
| 4,928,172 A | * | 5/1990 | Uehara et al. ................ | 348/69 |
| 5,007,408 A | * | 4/1991 | Ieoka .......................... | 600/109 |
| 5,177,605 A | * | 1/1993 | Takahashi et al. ............ | 348/65 |
| 6,117,071 A | * | 9/2000 | Ito et al. ..................... | 600/168 |
| 6,342,460 B1 | * | 1/2002 | Akimoto et al. .............. | 501/55 |
| 6,471,636 B1 | * | 10/2002 | Sano et al. .................. | 600/109 |
| 6,493,115 B1 | * | 12/2002 | Kanno et al. ................ | 358/538 |
| 2002/0175993 A1 | * | 11/2002 | Ueno et al. ................... | 348/68 |

* cited by examiner

Primary Examiner—John P. Leubecker
(74) Attorney, Agent, or Firm—Snider & Associates; Ronald R. Snider

(57) ABSTRACT

An endoscope includes a red component cut optical filter having a characteristic that a spectral transmittance becomes half at 630 nm and zero at 670 nm, for example between a light source and an infrared cut filter, to remove a long wavelength component mainly in a red band of illumination light. This restrains scattering of light on a long wavelength side of red light, and allows taking images of mucosa, blood vessels, and other tissue in good contrast in an object to be observed and satisfactorily observing them on a monitor. Further, reduction in light amount resulting from cutting a red component with the filter is eliminated by light amount control with an aperture and gain control of a signal.

8 Claims, 9 Drawing Sheets

INFRARED
CUT FILTER

EMBODIMENT

ENDOSCOPE HAVING RED COMPONENT CUT FILTER

BACKGROUND OF THE INVENTION

This application claims the priority of Japanese Patent Applications No. 2001-288182 filed on Sep. 21, 2001 and No. 2001-295270 filed on Sep. 27, 2001 which are incorporated herein by reference.

1. Field of the Invention

The present invention relates to an endoscope, and more particularly, to supply of illumination light and signal processing in an endoscope that allows observation of fine structure, enlarged by optical zooming, of blood vessels or the like of an object to be observed.

2. Description of the Related Art

An endoscope, for example, an electronic endoscope takes an image, by an image pickup device such as a CCD (Charge Coupled Device), of an object to be observed, captured via an objective optical system by applying illumination light, and displays an image of the object to be observed on a monitor or the like. Recently, a movable lens has been incorporated into the objective optical system, and the movable lens is moved back and forth by a zoom mechanism to optically enlarge the image of the object to be observed. The enlarged image is processed and displayed on the monitor or the like, and allows observation of details of a site to be observed.

By the above described endoscope, digestive organs in vivo are often observed, and it is important to observe blood vessels (blood capillaries) or other tissue near a surface of mucosa in vivo. Specifically, useful diagnosis information can be obtained from vascularization and spreading manner of the blood vessels, fine structure of the mucosa in vivo, or the like. However, there is a problem that hemoglobin in blood also exists in peripheral tissue, thus entire sites in vivo have redness to cause unclear distinction between the mucosa and the blood vessel, or other tissue.

Such unclear distinction between the mucosa and the blood vessel can be recognized by spectral reflectances mentioned below. FIG. 9A shows a spectral reflectance of normal gastric mucosa (wavelengths of 400 to 800 nm), FIG. 9B shows a spectral reflectance of human blood, FIG. 9C shows overlapped characteristic curves of the spectral reflectances of the normal gastric mucosa and the blood. As shown in FIG. 9C, a spectral reflectance curve $C_1$ of the normal gastric mucosa and a spectral reflectance curve $C_2$ of the blood cross near a wavelength of 600 nm. The spectral reflectance of the blood becomes significantly high over the wavelength of 600 nm.

FIG. 10 shows a depth that each color contained in illumination light reaches in a lower layer of the mucosa. The longer the wavelength of the light becomes from blue to red, or the longer the wavelength of red light becomes, more scattering occurs in the lower layer of the mucosa. The scattering of the long wavelength light prevents taking a good image of the blood vessels near the mucosa.

In the past, to avoid saturation of a CCD used as an image pickup device by infrared radiation, an infrared cut optical filter for cutting infrared radiation has been used. FIG. 11 shows an example of a spectral transmittance characteristic of a recent infrared cut filter, and this filter has a characteristic that the spectral transmittance becomes half near 660 nm and zero at 700 nm.

FIG. 12 shows spectral reflectances of the mucosa and the blood when using the above described infrared cut filter (corresponding to FIG. 9C). As shown in FIG. 12, this infrared cut filter cuts light in an infrared band according to a characteristic curve in FIG. 11. Specifically, a wavelength band from near 700 nm and higher is removed, and a long wavelength side of the spectral reflectance of the blood is also cut.

However, the infrared cut filter is simply for removing the infrared radiation, and as described above, scattering, below the mucosa, of a long wavelength component among red lights causes the image of the object to be observed to have redness, and contrast for sufficient distinction between the mucosa, the blood vessels, and other tissue cannot be obtained.

For the spectral reflectance characteristic in FIG. 12, an area $S_1$ surrounded by curves $C_1$ and $C_2$ of wavelengths from 400 nm to near 600 nm shows a component contributing to the contrast between the mucosa, the blood vessels, and other tissue in the image of the object to be observed, and an area $S_2$ surrounded by curves $C_1$ and $C_2$ of wavelengths near 600 nm and higher shows a component causing light scattering in the lower layer of the mucosa and reducing the contrast between the mucosa and the blood, or the like, and a size of the area $S_2$ becomes a problem.

SUMMARY OF THE INVENTION

The present invention has been achieved in view of the above described problem, and has an object to provide an endoscope capable of improving redness of an image to be observed, observing mucosa, blood vessels, and other tissue in good contrast, and keeping brightness and sharpness.

To achieve the above described object, an endoscope according to the invention includes: a light source for emitting light; a light guide for guiding the light from the light source to a tip of a scope as illumination light; an objective optical system for capturing an image of an object to be observed based on the illumination light irradiated from the tip of the scope; and a red component cut optical filter for cutting a long wavelength side in a red band of the illumination light. The red component cut optical filter may be provided between a light source of the light source and a condenser, or at an entrance end of the light guide.

The red component cut optical filter preferably has a characteristic that a spectral transmittance of the illumination light becomes zero near 670 nm. In this case, a half value of the spectral transmittance is, for example, 630±10 nm. The invention is preferably applied to an endoscope including an optical enlargement mechanism for obtaining an optically enlarged image by moving a movable lens of the objective optical system.

According to a configuration of the invention, a red component cut optical filter having a characteristic that, for example, a spectral transmittance becomes half at 630 nm and zero at 670 nm is provided between a light source lamp and an entrance end of a light guide, thereby removing a long wavelength component mainly in a red band of illumination light. This restrains scattering of red light of the object to be observed in a lower layer of mucosa, and allows capturing mucosa, blood vessels, and other tissue in good contrast in an observed image (or an enlarged image) by an image pickup device.

An endoscope according to another aspect of the invention includes: a light source for emitting light; a light guide for guiding the light from the light source to a tip of a scope as illumination light; an objective optical system for capturing an image to be observed based on the illumination light irradiated from the tip of the scope; an image pickup device for taking the image of the object to be observed, captured by the objective optical system; a red component cut optical filter, inserted into a supply line of the illumination light, for cutting a long wavelength side in a red band of the illumination light; a light amount control circuit for adjusting an output amount of the illumination light to keep constant brightness of the image of the object to be observed based on metering information obtained from output of the image pickup device; a gain control circuit for controlling to keep a constant level of an image signal based on the metering information; and a control circuit for operating the light amount control circuit, operating the gain control circuit when the light amount is insufficient even if a maximum value of the light amount control is reached, and eliminating reduction in the light amount by the red component cut optical filter.

The control circuit determines whether the red component cut optical filter is set in the endoscope or not, and controls to operate the light amount control circuit when the red component cut optical filter is set, operate the gain control circuit when the light amount is insufficient even if the light amount control is performed, and operate only the light amount control circuit when the red component cut optical filter is not set.

According to a configuration of another aspect of the invention, when the red component cut optical filter is not set, light amount control is performed using, for example, an aperture, while when the filter is set, the light amount control using the aperture is performed, and also gain control of an image signal is performed when it is dark even if the aperture is opened to a maximum. Thus, fine structure of the blood vessels or the like can be clearly observed in a bright image of the object to be observed.

DETAILED DESCRIPTION OF THE PREFERRED EMBODIMENTS

First Embodiment

Figure 1:
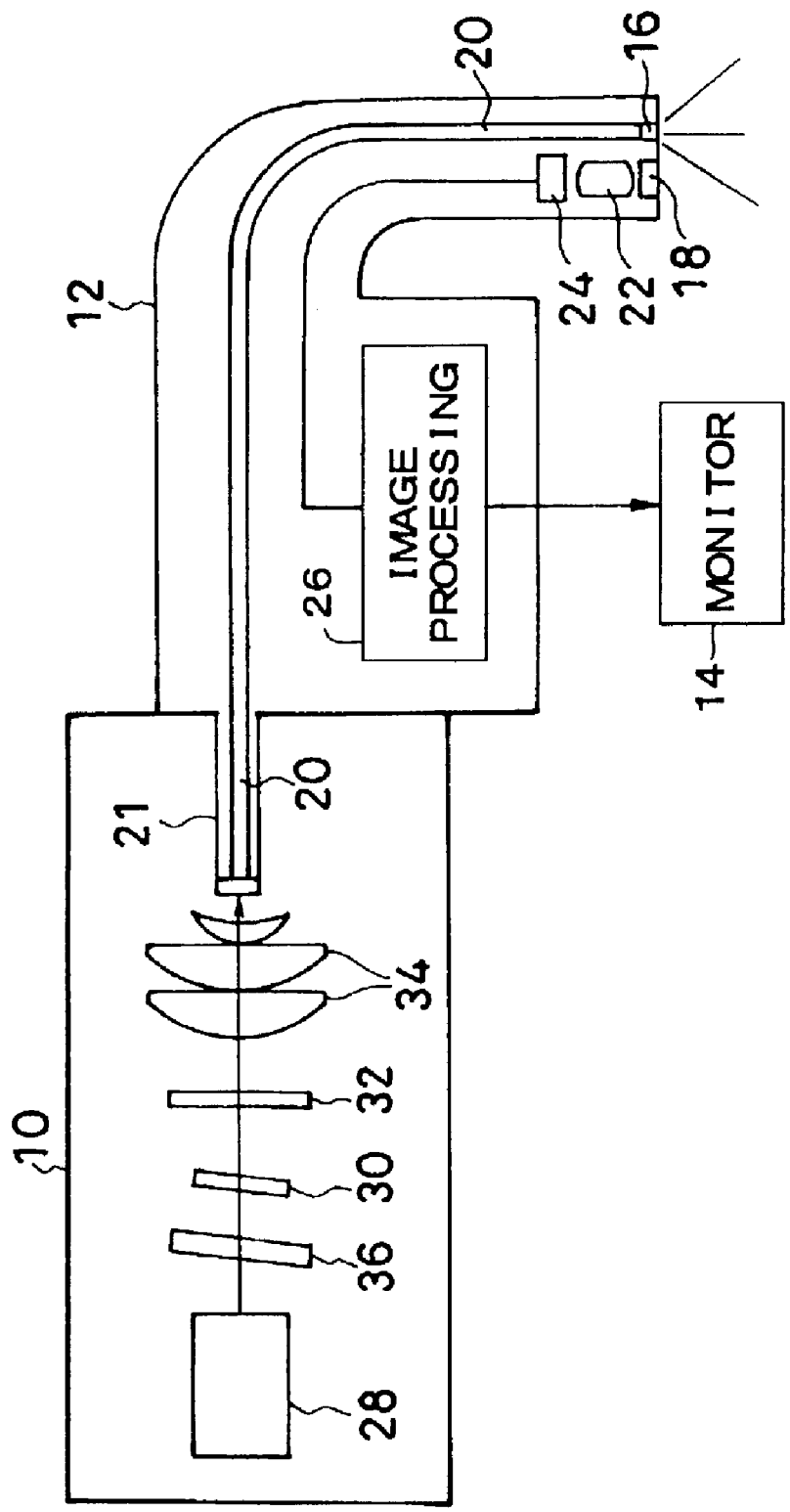
FIG. 1 shows a main configuration of an electronic endoscope according to a first embodiment of the invention.

FIG. 1 shows a configuration of a part of an electronic endoscope according to a first embodiment. The electronic endoscope includes a light source 10, a scope and processor unit 12, and a monitor 14. In FIG. 1, the scope and processor unit 12 has an illumination window 16 and an observation window 18 at a tip of a scope, and a light guide 20 connects to the illumination window 16 and extends to a connector 21 to connect to the light source 10. To the observation window 18, a CCD 24 that is an image pickup device optically connects via an objective optical system 22.

An electronic endoscope having a zoom mechanism includes a movable lens, as a part of the objective optical system 22, that is moved back and forth such as by an unshown rotating linear transfer member. The linear transfer member is driven by, for example, a motor, and the back and forth movement of the movable lens provides an optically enlarged image.

After the CCD 24, an image processing circuit 26 is connected that performs correlated double sampling and then image processing such as gamma correction as a digital signal, and a brightness signal and a color difference signal output from the image processing circuit 26 are fed to the monitor 14.

In the light source 10, a light source 28 that is a xenon lamp or a halogen lamp, an infrared cut filter 30, a light amount control shutter 32, and a condenser 34 are arranged, and light from the condenser 34 is output to an entrance end of the light guide 20. A red component cut filter 36 is inserted between the light source 28 and the infrared cut filter 30 such that a filter surface of the red component cut filter 36 is substantially vertical to an optical axis. At this time, it is desirable that a light beam emitted from the light source 28 is substantially horizontal to the optical axis. The infrared cut filter 30 may or may not be provided.

Figure 2:
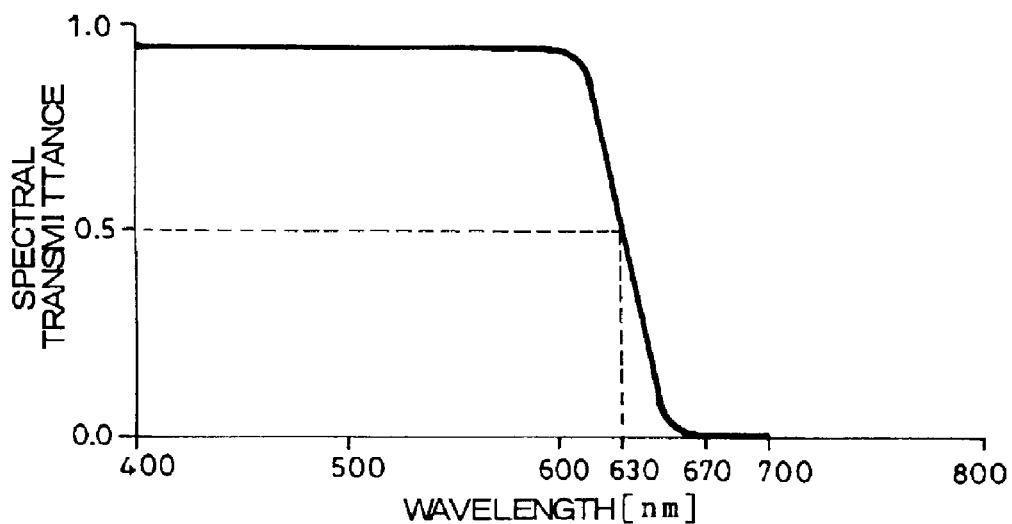
FIG. 2 shows a characteristic of a spectral transmittance of a red component cut filter (optical) filter according to the embodiment.

FIG. 2 shows a spectral transmittance of the red component cut filter 36, and the red component cut filter 36 has a characteristic that the spectral transmittance becomes zero at a wavelength of 670 nm and half at a wavelength of 630 nm. When the spectral transmittance is zero at the wavelength of 670 nm, a half value is 630±10 nm. For the red component cut filter 36, the spectral transmittance may become zero at wavelengths near 670 nm and lower. Thus, a filter may be used having a characteristic that a spectral transmittance becomes zero at 650 nm or the like with substantially the same half value.

The first embodiment is configured as described above, and the red component cut filter 36 cuts more than half of wavelength components of 630 nm and higher in output light from the light source 28.

Figure 3:
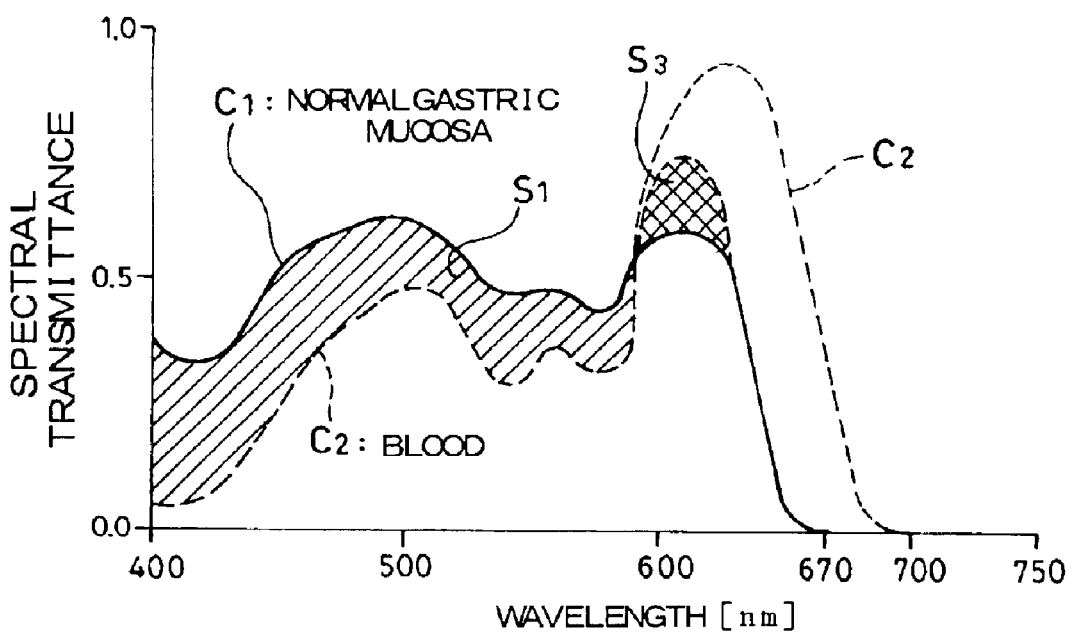
FIG. 3 shows characteristics of spectral transmittances of normal gastric mucosa and blood when using a red component cut filter of the embodiment.
Figure 9A:
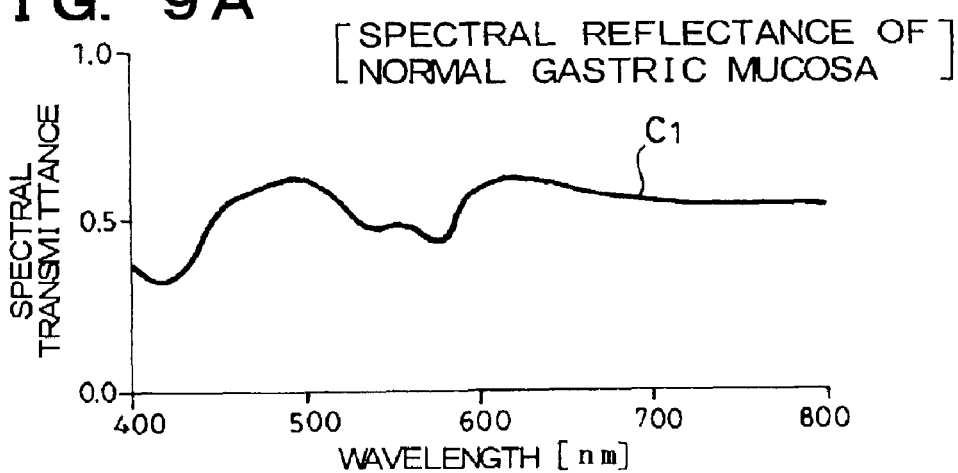
FIG. 9A shows a spectral reflectance characteristic of normal gastric mucosa (wavelengths of 400 to 800 nm)
Figure 9B:
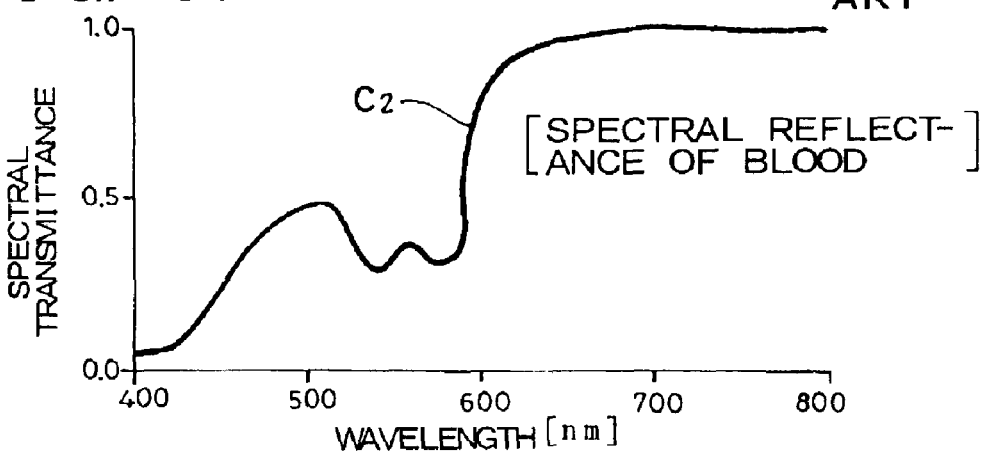
FIG. 9B shows a spectral reflectance characteristic of human blood.
Figure 9C:
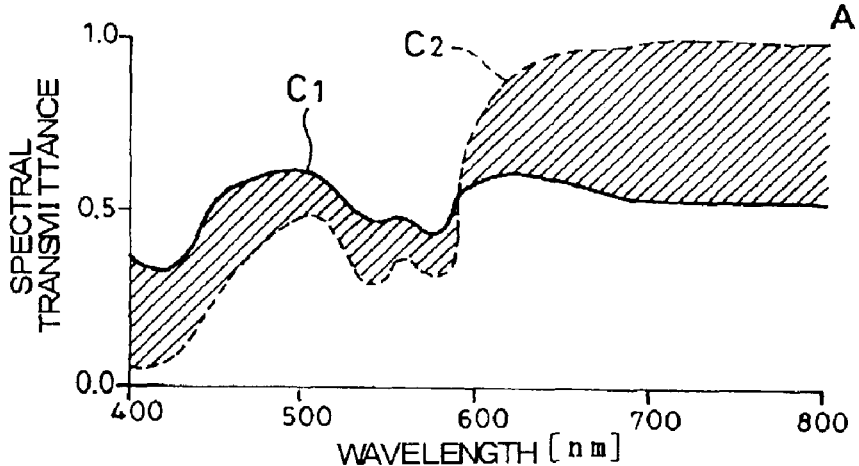
FIG. 9C shows overlapped characteristic curves of the spectral reflectances of the normal gastric mucosa and the blood.
Figure 10:
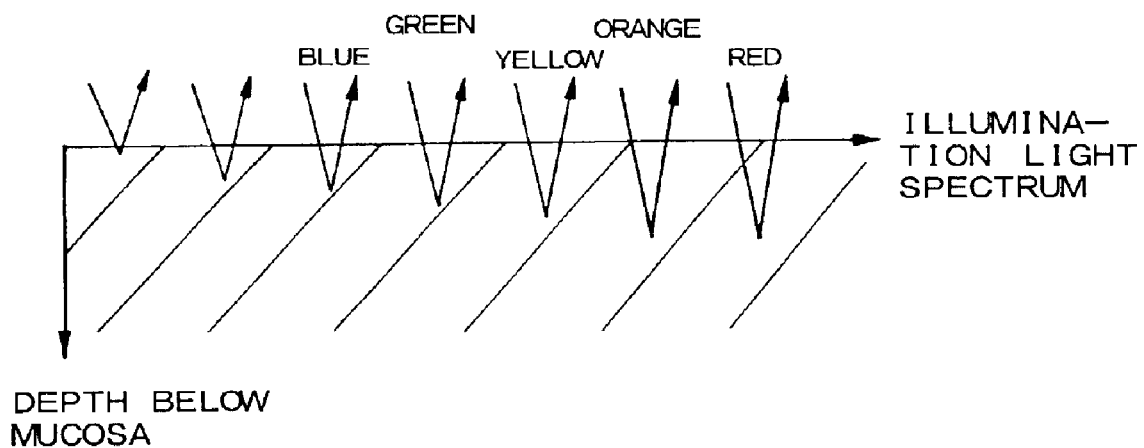
FIG. 10 illustrates depths that color components of illumination light reach in a lower layer of the mucosa.

FIG. 3 shows spectral transmittances of normal gastric mucosa and blood when using the red component cut filter 36 (corresponding to FIG. 9C). According to the embodiment, as shown in FIG. 3, light in a red band is partially cut according to a characteristic curve in FIG. 2. Specifically, a wavelength band from near 670 nm and higher is removed, and a long wavelength side of red light is cut in the spectral reflectance of the blood.

Figure 12:
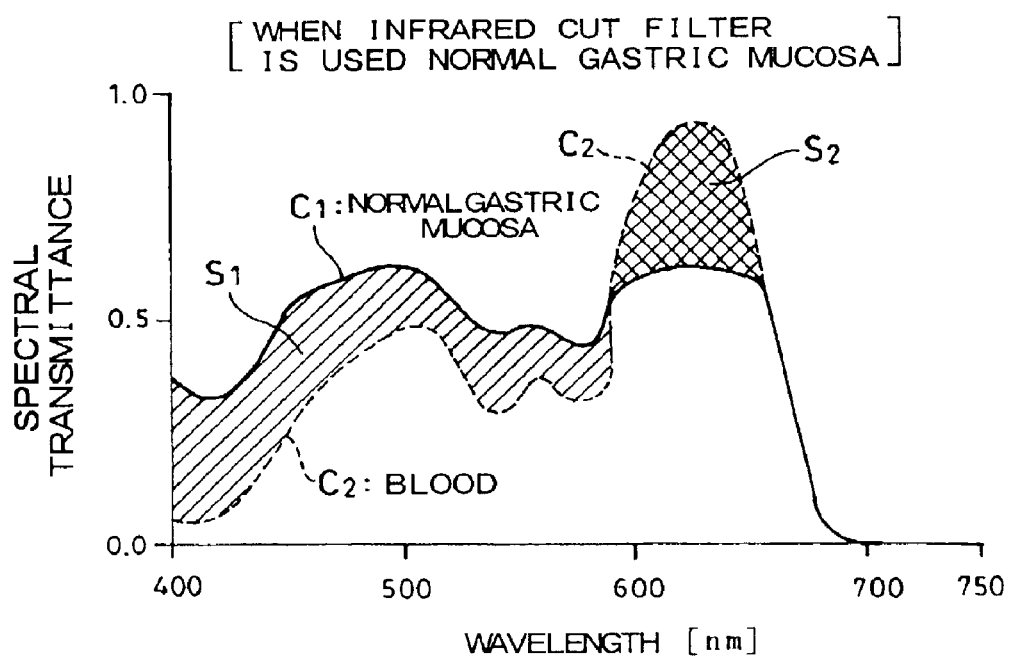
FIG. 12 shows characteristics of spectral reflectances of the normal gastric mucosa and the blood when using the infrared cut filter in FIG. 11.

Comparison between FIG. 3 and FIG. 12 reveals that an area $S_1$ showing a component that contributes to contrast between the mucosa and the blood in an image of an object to be observed remains, while an area $S_3$ surrounded by curves $C_1$ and $C_2$ that causes light scattering in a lower layer of the mucosa is significantly reduced compared to an area $S_2$ of a conventional example in FIG. 12. Thus, the red component cut filter 36 removes the wavelength component (on the long wavelength side) that causes reduction in contrast between the mucosa and the blood, and secures a minimum red component forming a color image, thus allowing display of the mucosa, the blood, and other tissue in good contrast.

Figure 4:
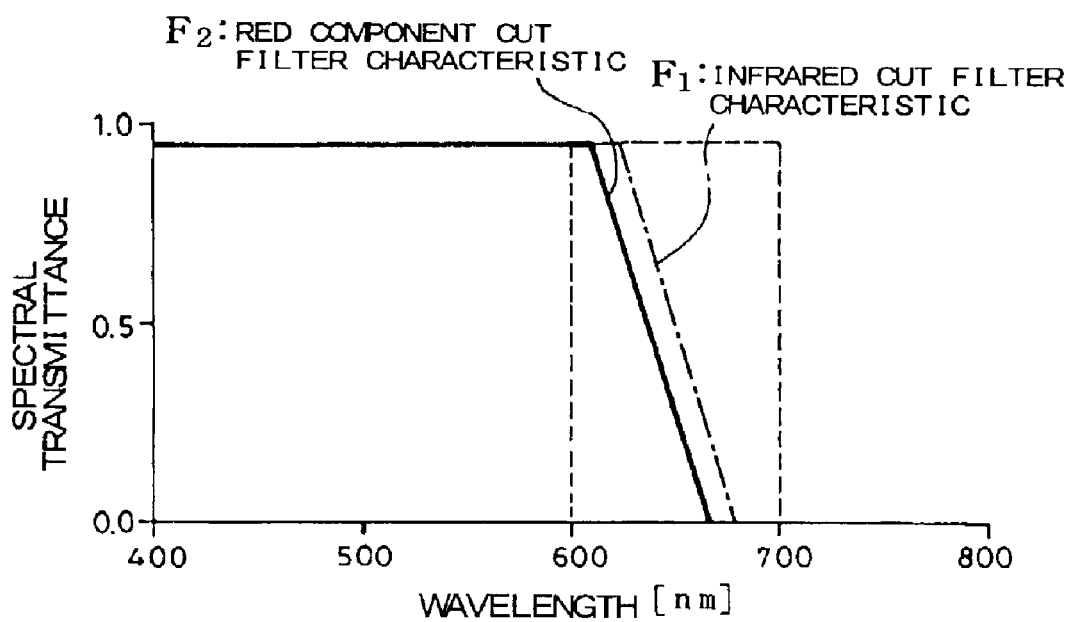
FIG. 4 shows comparison between spectral transmittance characteristics of the red component cut filter of the embodiment and an infrared cut (optical) filter.
Figure 5A:
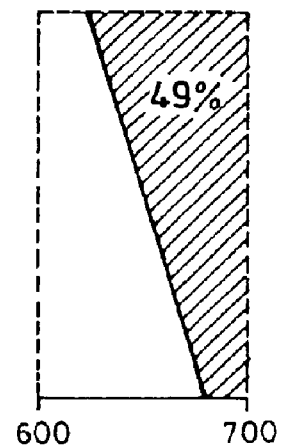
FIG. 5A shows an amount of energy cut of the infrared cut filter having a characteristic in FIG. 11.
Figure 5B:
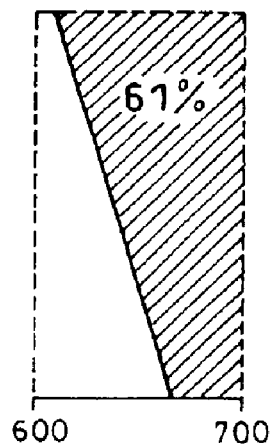
FIG. 5B shows an amount of energy cut of the red component cut filter of the embodiment.
Figure 11:
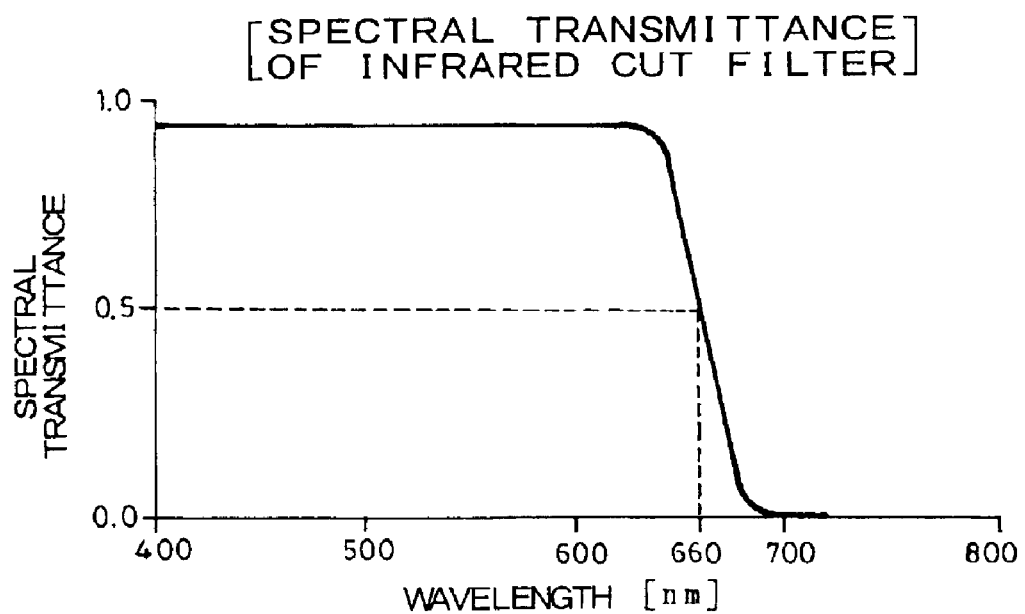
FIG. 11 shows a characteristic of a spectral transmittance of a conventional infrared cut filter.

FIG. 4 and FIG. 5 show filter characteristics and amounts of energy cut of the infrared cut filter illustrated in FIG. 11 and the red component cut filter of the embodiment. As shown in FIG. 4, the characteristic of the infrared cut filter is denoted by $F_1$, and the characteristic of the red component cut filter 36 is denoted by $F_2$. Comparing the amounts of energy within a range of wavelengths of 600 to 700 nm, the infrared cut filter cuts 49% energy by removing the long wavelength side as shown in FIG. 5A, and the red component cut filter 36 of the embodiment cuts 61% energy as shown in FIG. 5B.

Specifically, for the amount of energy within the range of wavelengths of 600 to 700 nm, redness is gradually improved at the amount of cut of more than 50%, and good contrast for distinction between the mucosa, the blood, and other tissue can be obtained at around 60%. Of course, more than 60% is acceptable.

The light output through the red component cut filter 36 is output to the entrance end of the light guide 20 (connector 21) through the condenser 34 in FIG. 1, and applied to the object to be observed via the light guide 20 as the illumination light. Next, when the image of the object to be observed is captured by the CCD 24 via the objective optical system 22, the image processing circuit 26 performs signal processing to display the image of the object to be observed on the monitor 14. At this time, operating the optical zoom mechanism causes the enlarged image to be displayed on the monitor 14. According to the embodiment, the redness as in the conventional case is improved in the image displayed on the monitor 14, and the mucosa, the blood, and other tissue can be observed in good contrast.

Second Embodiment

Figure 6:
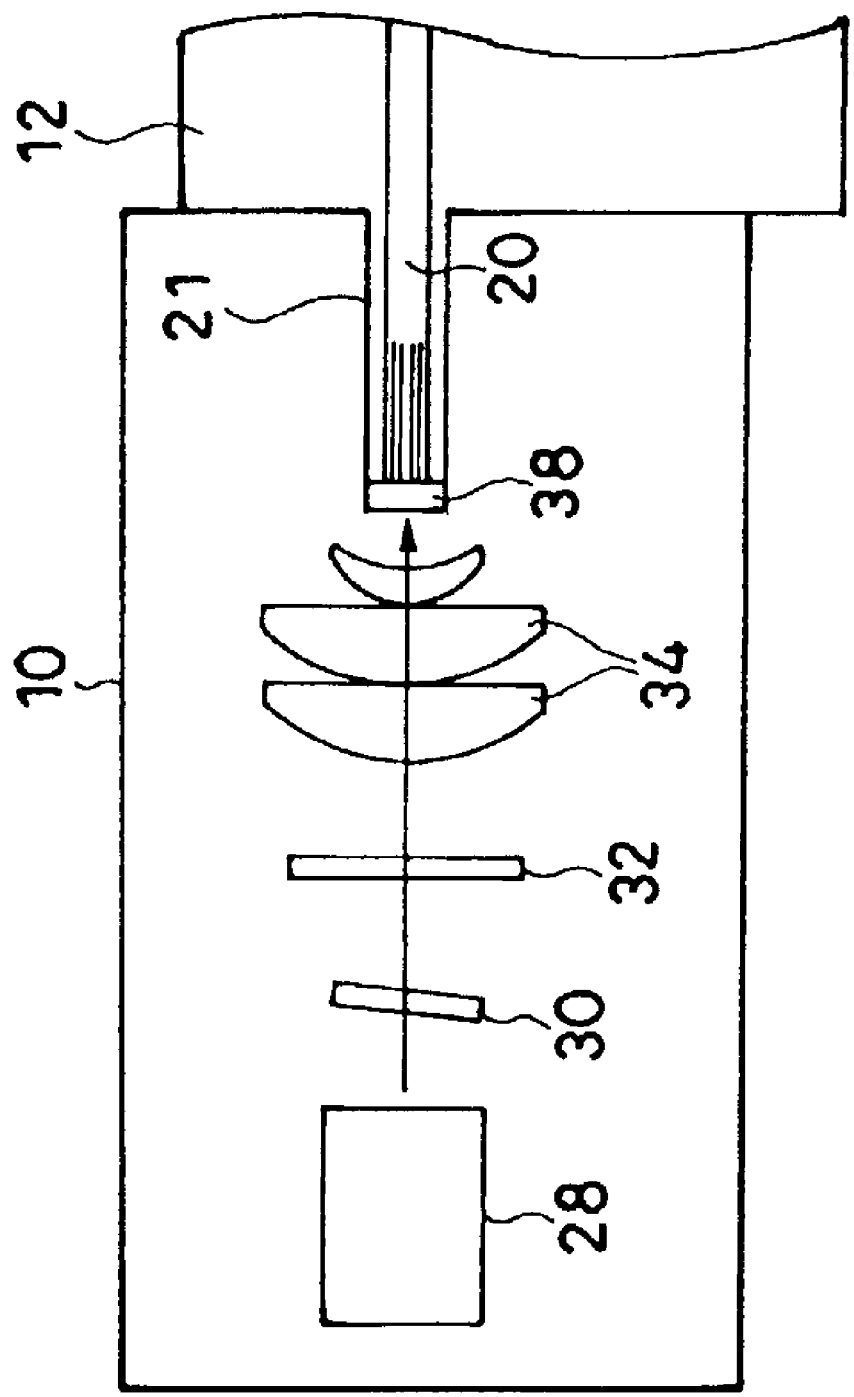
FIG. 6 shows a main configuration of an electronic endoscope according to a second embodiment of the invention.

FIG. 6 shows a configuration of a second embodiment in which a red component cut filter is placed in a position different from the position in the first embodiment. As shown in FIG. 6, in the second embodiment, the red component cut filter is not placed immediately after a light source 28, but a red component cut filter member 38 in which a coating for cutting a red component is applied across an optical plate member is provided as a light entrance end member of a light guide 20 in a connector 21 in a scope and processor unit 12.

The red component cut filter member 38 has a filter characteristic like the filter characteristic in FIG. 2, and the second embodiment allows obtaining the advantage explained in FIG. 3. The red component cut filter may be provided at other places, for example, at a midway through the light guide 20, or a light emitting end of the light guide 20 at a tip of a scope.

As described above, the first and second embodiments restrain the scattering of the light on the long wavelength side of the red light, improve the redness of the image of the object to be observed, and allow taking images of and observing the mucosa, the blood vessels, and other tissue in good contrast.

Third Embodiment

Figure 7:
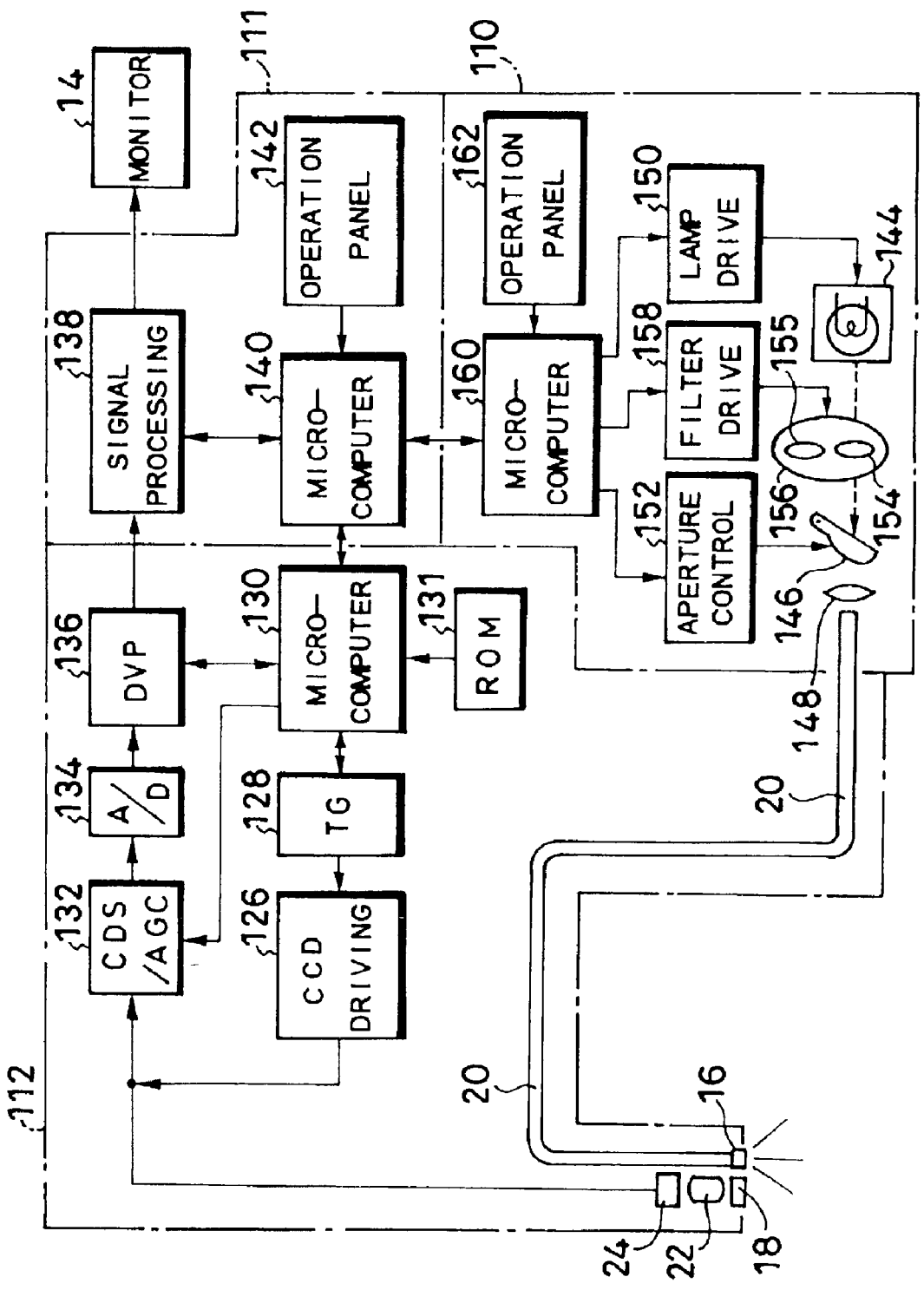
FIG. 7 shows a main configuration of an electronic endoscope according to a third embodiment of the invention.

FIG. 7 shows a main configuration of an electronic endoscope according to a third embodiment. The electronic endoscope includes a light source 110, a processor unit 111, a scope 112, and a monitor 14. Like the fist embodiment, the light source 110 connects to a light guide 20 connecting to an illumination window 16 at a tip of the scope 112, and to an observation window 18, a CCD 24 optically connects via an objective optical system 22.

The CCD 24 is driven and controlled by a CCD drive circuit 126, to which a scope side microcomputer 130 connects via a timing generator (TG) 128. To the microcomputer 130, a ROM 131 connects that stores various data for image processing, and limit value data of gain control when a red component cut filter (154) described later is used.

A CDS (correlated double sampling)/AGC (auto gain control) circuit 132 is provided on an output side of the CCD 24, and amplifies an image signal to match a control value received from the microcomputer 130. After the CDS/AGC circuit 132, a DVP (digital video processor) 136 is provided via an A/D converter 134, and the DVP 136 performs image processing such as gamma correction of a digital image signal to form, for example, a brightness signal and a color different signal. The DVP 136 meters an amount of light captured by the CCD 24 from the image signal (brightness signal), and controls to keep constant brightness of the image based on the metered value.

The processor unit 111 has a signal processing circuit 138 to input the output of the DVP 136, and the signal processing circuit 138 performs signal processing for outputting to the monitor 14. A processor side microcomputer 140 connects to the signal processing circuit 138, and an operation signal from a front operation panel 142 is fed to the microcomputer 140.

The light source 110 includes a light source (lamp) 144, an optical aperture 146, a condenser 148, a light source drive circuit 150 for driving the light source 144, and an aperture control circuit 152 for controlling an opening of the aperture 146.

Between the light source 144 and the aperture 146, a rotating filter 156 having a red component cut filter 154 and an infrared cut filter 155 is provided, and the rotating filter 156 is driven by a filter drive circuit 158. The light source 110 also includes a microcomputer 160 for controlling the filter drive circuit 158 or the like, and the microcomputer 160 inputs an operation signal from a front operation panel 162 and transmits data between the microcomputer 160 and other microcomputers 130, 140.

The microcomputer 160 performs light amount control by the aperture 146, setting the filters 154, 155, and gain control according to insufficient amount of light. Specifically, the microcomputer 160 inputs a metering signal formed by the DVP 136 of the scope 112, controls the opening of the aperture 146 via the aperture control circuit 152 to keep constant brightness of the image, rotates the rotating filter 156 via the filter drive circuit 158 based on operation of the front operation panel 162, and sets either of the red component cut filter 154 or the infrared cut filter 155. As the red component cut filter 154, a filter is used having a characteristic that a spectral transmittance becomes half at 630 nm (±10 nm) and zero at 670 nm as show in FIG. 2.

Further, the microcomputer 160 performs auto gain control by the CDS/AGC circuit 132 via the microcomputer 130 when predetermined brightness cannot be obtained even if a maximum opening of the aperture 146 is reached. Specifically, if the metering signal is controlled to be fed to the CDS/AGC circuit 132 with a maximum position of the aperture 146 kept, the CDS/AGC circuit 132 amplifies the image signal to keep constant brightness of the image based on the metering signal. In the auto gain control, a gain limit value stored in the ROM 131 is read, and the gain is controlled not to exceed the limit value to prevent reduction in sharpness of the image.

The third embodiment is configured as described above, and when the red component cut filter 154 is used, as shown in FIG. 3, a wavelength band from near 670 nm and higher is removed according to the characteristic curve in FIG. 2, and a long wavelength side of red light is cut in the spectral reflectance of the blood. This removes the wavelength component that causes reduction in contrast between the mucosa and the blood, and secures a minimum red component forming a color image, thus allowing display of the mucosa, the blood, and other tissue in good contrast.

In FIG. 7, the light output through the red component cut filter 154 is applied to an object to be observed via the light guide 20 as the illumination light, thus an image of the object to be observed is captured by the CCD 24 via the objective optical system 22. In the CCD 24, accumulated charge per pixel is read by the CCD drive circuit 126, and the output signal of the CCD 24 is subjected to correlated double sampling by the CDS/AGC circuit 132, and then to signal processing in the DVP 136 and the signal processing circuit 138 to display an enlarged image of the object to be observed on the monitor 14. In such image processing, the light amount control is performed to keep constant brightness of the image.

Figure 8:
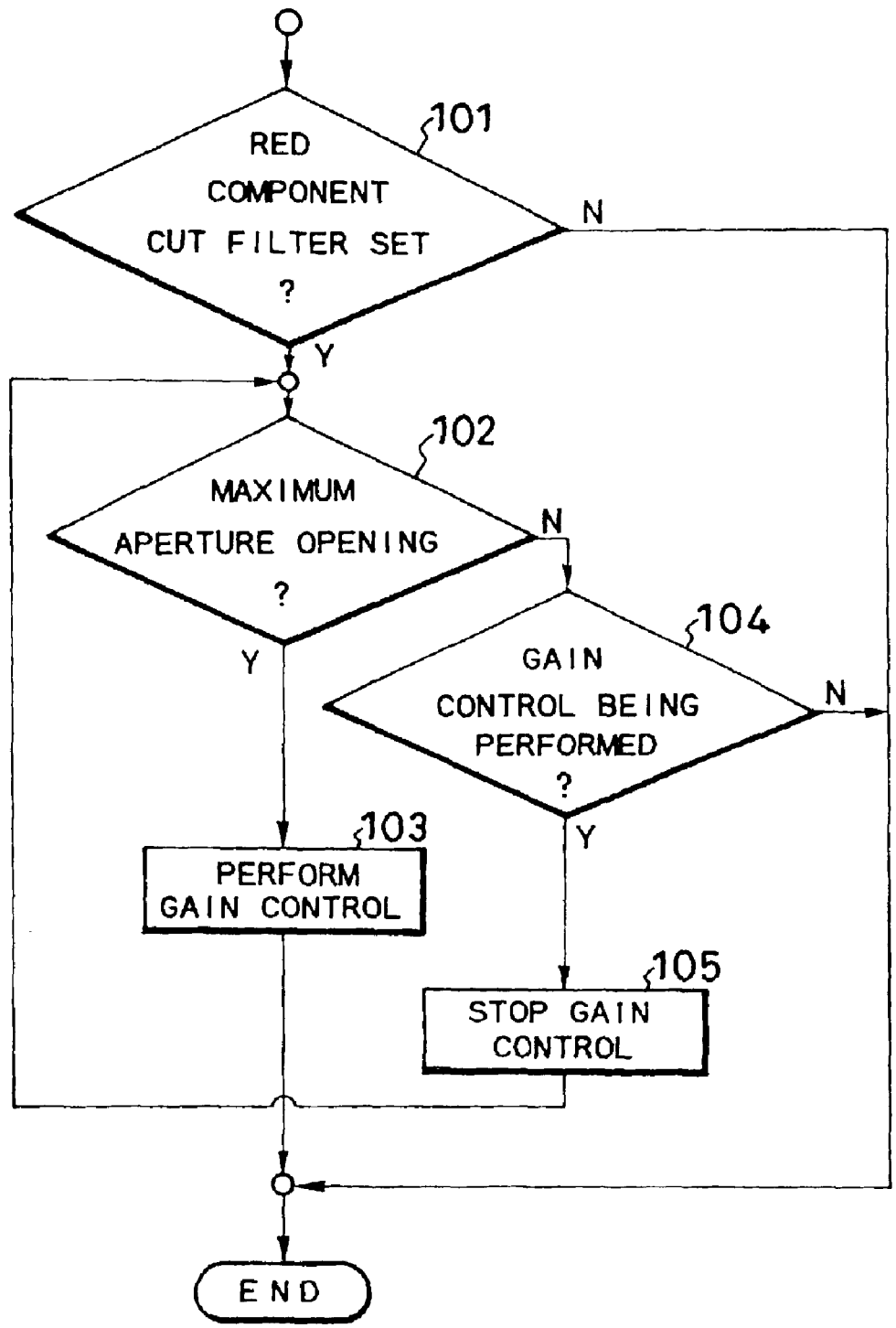
FIG. 8 shows a flowchart of operation by a microcomputer in the third embodiment.

FIG. 8 shows operation of the light amount control via the microcomputers 130, 140, and 160. In Step 101, it is determined whether the red component cut filter 154 is set or not. The filter set condition is recognized by the microcomputer 160, and when the red component cut filter 154 is set to be Y (YES), the process moves to Step 102. In Step 102, it is determined whether the opening of the aperture 146 is maximum or not, and when the aperture 146 is set to the maximum opening position to be Y, the gain control for insufficient light amount is performed in Step 103.

Specifically, the microcomputer 160 controls the opening of the aperture 146 based on the metering signal obtained by the DVP 136 to keep constant brightness of the image, but when the light amount is insufficient even if the maximum opening of the aperture 146 is reached, a gain control signal corresponding to the metering signal is fed to the CDS/AGC circuit 132 by the microcomputer 130, thereby amplifying the image signal. This allows satisfactorily supplying light of the amount corresponding to the amount of the red component light cut by the red component cut filter 154. In the gain control, the image signal is not gained up (amplified) to more than the limit value, thus preventing coarse image.

When the opening of the aperture 146 is not set to the maximum but to be N (NO) in Step 102, it is determined whether the gain control is being performed in Step 104, and when Y in Step 104, the gain control for insufficient light is stopped in Step 105. Both the aperture control and the gain control allow constant brightness of the image to be kept, and the light amount control by the aperture 146 has an effect of reducing noise to keep sharpness of the image. The auto gain control prevents reduction in sharpness by not gaining up to more than the limit value.

When a light source 110 having a red component cut filter 154 only mounted, or a scope 112 having the red component cut filter mounted to a light guide connector is used unlike the configuration of the third embodiment, a mounting and setting condition of the red component cut filter is detected and determined by transmitting information between the microcomputers to obtain the same operation and advantage as described above.

In the third embodiment, the light amount control of the illumination light by the aperture 146 is described, but as the light amount control, a method of controlling a lighting voltage of the light source 144 using the lamp drive circuit 150 may be used. Performing the gain control when the light amount is insufficient even if a lamp lighting voltage is set to a maximum offers the same advantage.

As described above, the third embodiment eliminates reduction in the light amount to provide a bright and sharp image even when the long wavelength side in the red band is cut, improves the redness of the image of the object to be observed, and allows taking images of and observing the mucosa, the blood vessel, and other tissue in good contrast.

What is claimed is:

1. An endoscope comprising:
   a light source for emitting light;
   a light guide for guiding the light from the light source to a tip of a scope as illumination light;
   an objective optical system for capturing an image of an object to be observed based on the illumination light irradiated from the tip of said scope; and
   a red component cut optical filter for cutting a long wavelength side in a red band of said illumination light, disposed between said light source and said light guide;
   wherein said red component cut optical filter has a characteristic that a spectral transmittance of said illumination light becomes half at wavelengths 630±10 nm and zero at wavelengths near 670 nm.

2. The endoscope according to claim 1, wherein said red component cut optical filter cuts more than 50% of an amount of energy within a range of wavelengths of 600 to 700 nm.

3. The endoscope according to claim 1, further comprising an optical enlargement mechanism for obtaining an optically enlarged image by moving a movable lens of the objective optical system.

4. The endoscope according to claim 1, wherein said red component cut optical filter is provided at an entrance end of the light guide.

5. An endoscope comprising:
   a light source for emitting light;
   a light guide for guiding the light from the light source to a tip of a scope as illumination light;
   an objective optical system for capturing an image of an object to be observed based on the illumination light irradiated from the tip of said scope;
   an image pickup device for taking the image of the object to be observed, captured by the objective optical system;
   a red component cut optical filter, inserting into a supply line of said illumination light, for cutting a long wavelength side in a red band of the illumination light so as to observe mucosa and blood vessels in good contrast;
   a light amount control circuit for adjusting an output amount of said illumination light to keep constant brightness of the image of the object to be observed based on metering information obtained from output of the image pickup device;
   a gain control circuit for controlling to keep a constant level of an image signal based on said metering information; and
   a control circuit for operating said light amount control circuit, operating said gain control circuit when a light amount is insufficient even if a maximum value of the light amount control is reached, and eliminating reduction in the light amount by said red component cut optical filter;

wherein said red component cut optical filter has a characteristic that a spectral transmittance of said illumination light becomes half at wavelengths 630±10 nm and zero at wavelengths near 670 nm.

6. The endoscope according to claim 5, wherein said control circuit determines whether said red component cut optical filter is set in the endoscope or not, and controls to operate said light amount control circuit when the red component cut optical filter is set, operate said gain control circuit when the light amount is insufficient even if the light amount control is performed, and operate only said light amount control circuit when the red component cut optical filter is not set.

7. The endoscope according to claim 5, wherein said red component cut filter is mounted to a rotating filter together with an infrared cut filter, and either of said filters is set by rotary switching of the rotating filter.

8. The endoscope according to claim 5, wherein said gain control circuit does not increase gain to more than a limit amount to prevent reduction in sharpness of the image.

* * * * *